US010582969B2

(12) United States Patent
Couture et al.

(10) Patent No.: US 10,582,969 B2
(45) Date of Patent: Mar. 10, 2020

(54) PATIENT-SPECIFIC INSTRUMENTATION FOR IMPLANT REVISION SURGERY

(71) Applicant: ZIMMER, INC., Warsaw, IN (US)

(72) Inventors: Pierre Couture, Montreal (CA); Jean-Sebastien Merette, Mont-St-Hilaire (CA)

(73) Assignee: ZIMMER, INC., Warsaw, IN (US)

( * ) Notice: Subject to any disclaimer, the term of this patent is extended or adjusted under 35 U.S.C. 154(b) by 740 days.

(21) Appl. No.: 15/205,777

(22) Filed: Jul. 8, 2016

(65) Prior Publication Data
US 2017/0007331 A1 Jan. 12, 2017

Related U.S. Application Data

(60) Provisional application No. 62/189,941, filed on Jul. 8, 2015.

(51) Int. Cl.
A61B 34/10 (2016.01)
A61F 2/46 (2006.01)
(Continued)

(52) U.S. Cl.
CPC .......... A61B 34/10 (2016.02); A61B 17/155 (2013.01); A61B 17/157 (2013.01);
(Continued)

(58) Field of Classification Search
CPC .............. A61B 34/10; A61B 2034/101; A61B 2034/102; A61B 2034/105;
(Continued)

(56) References Cited

U.S. PATENT DOCUMENTS

| 4,841,975 A | 6/1989 | Woolson |
| 5,098,383 A | 3/1992 | Hemmy et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Hofmann et al, "Natural-Knee II System", Intermedics Orthopedics, Austin, TX, 1995.

Primary Examiner — Matthew J Lawson
(74) Attorney, Agent, or Firm — Norton Rose Fulbright Canada LLP

(57) ABSTRACT

A method for creating a model of a patient-specific instrumentation jig for implant revision includes obtaining an image of part of a patient bone and of an implanted implant on the bone. A reference anchor surface(s) is identified on the bone from the image, to receive a guide reference. An implant abutment surface is determined on the implanted implant. A virtual reference jig model is generated using the identified reference anchor surface and the determined implant abutment surface, and has a contact surface corresponding to the determined implant abutment surface for complementary connection with the determined implant abutment surface, a guide interfacing portion to guide a planting of the guide reference in the reference anchor surface, and a patient-specific geometry between the contact surface and the guide interfacing portion, to position and/or orient the guide interfacing portion relative to the reference anchor surface.

11 Claims, 8 Drawing Sheets

(51) Int. Cl.
*A61B 17/15* (2006.01)
*A61B 17/17* (2006.01)
*A61B 17/56* (2006.01)

(52) U.S. Cl.
CPC .......... *A61B 17/1764* (2013.01); *A61F 2/461* (2013.01); *A61B 17/1778* (2016.11); *A61B 2017/568* (2013.01); *A61B 2034/102* (2016.02); *A61F 2002/4687* (2013.01)

(58) Field of Classification Search
CPC ............ A61B 2034/108; A61B 17/155; A61B 17/1757; A61F 2/461
See application file for complete search history.

(56) References Cited

U.S. PATENT DOCUMENTS

| | | |
|---|---|---|
| 5,490,854 A | 2/1996 | Fisher et al. |
| 5,768,134 A | 6/1998 | Swaelens et al. |
| 5,871,018 A | 2/1999 | Delp et al. |
| 5,916,219 A | 6/1999 | Matsuno et al. |
| 7,357,057 B2 | 4/2008 | Chiang |
| 7,468,075 B2 | 12/2008 | Lang et al. |
| 7,510,557 B1 | 3/2009 | Bonutti |
| 7,534,263 B2 | 5/2009 | Burdulis |
| 7,618,451 B2 | 11/2009 | Berez et al. |
| 7,634,119 B2 | 12/2009 | Tsougarakis et al. |
| 7,717,956 B2 | 5/2010 | Lang |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,806,897 B1 | 10/2010 | Bonutti |
| 7,967,868 B2 | 6/2011 | White et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,070,752 B2 | 12/2011 | Metzger et al. |
| 8,077,950 B2 | 12/2011 | Tsougarakis et al. |
| 8,083,745 B2 | 12/2011 | Lang et al. |
| 8,092,465 B2 | 1/2012 | Metzger et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,133,234 B2 | 3/2012 | Meridew et al. |
| 8,160,345 B2 | 4/2012 | Pavlovskaia et al. |
| 8,175,683 B2 | 5/2012 | Roose |
| 8,221,430 B2 | 7/2012 | Park et al. |
| 8,234,097 B2 | 7/2012 | Steines et al. |
| 8,241,293 B2 | 8/2012 | Stone et al. |
| 8,282,646 B2 | 10/2012 | Schoenefeld et al. |
| 8,298,237 B2 | 10/2012 | Schoenefeld |
| 8,337,501 B2 | 12/2012 | Fitz et al. |
| 8,337,507 B2 | 12/2012 | Lang et al. |
| 8,343,218 B2 | 1/2013 | Lang et al. |
| 8,366,771 B2 | 2/2013 | Burdulis et al. |
| 8,377,129 B2 | 2/2013 | Fitz et al. |
| 8,439,926 B2 | 5/2013 | Bojarski et al. |
| 8,460,304 B2 | 6/2013 | Fitz et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski |
| 8,585,708 B2 | 9/2013 | Fitz et al. |
| 8,545,569 B2 | 10/2013 | Fitz et al. |
| 8,551,099 B2 | 10/2013 | Lang |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 2003/0055502 A1 | 3/2003 | Lang et al. |
| 2003/0216669 A1 | 11/2003 | Lang et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2005/0055028 A1 | 3/2005 | Haines |
| 2005/0234461 A1 | 10/2005 | Burdulis et al. |
| 2005/0267584 A1 | 12/2005 | Burdulis et al. |
| 2006/0111722 A1 | 5/2006 | Bouadi |
| 2007/0083266 A1 | 4/2007 | Lang |
| 2007/0100462 A1 | 5/2007 | Lang et al. |
| 2007/0156171 A1 | 7/2007 | Lang et al. |
| 2007/0157783 A1 | 7/2007 | Chiang |
| 2007/0198022 A1 | 8/2007 | Lang et al. |
| 2007/0226986 A1 | 10/2007 | Park et al. |
| 2007/0233141 A1 | 10/2007 | Park et al. |
| 2007/0233269 A1 | 10/2007 | Steines et al. |
| 2007/0250169 A1 | 10/2007 | Lang |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0195216 A1 | 8/2008 | Philipp |
| 2008/0243127 A1 | 10/2008 | Lang et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0024131 A1 | 1/2009 | Metzgu et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0222014 A1 | 9/2009 | Bojarski et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |

(56) References Cited

U.S. PATENT DOCUMENTS

| | | |
|---|---|---|
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0025348 A1* | 1/2014 | Abiven ............ A61B 17/155 703/1 |
| 2014/0029814 A1 | 1/2014 | Fitz et al. |
| 2014/0031826 A1 | 1/2014 | Bojarski et al. |

(56) References Cited

U.S. PATENT DOCUMENTS

| | | | |
|---|---|---|---|
| 2014/0039631 A1 | 2/2014 | Bojarski et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0086780 A1 | 3/2014 | Miller et al. | |
| 2014/0107655 A1 | 4/2014 | Song | |
| 2014/0208578 A1* | 7/2014 | Linderman | A61F 2/30756 29/592 |
| 2014/0257309 A1* | 9/2014 | Aram | A61B 17/154 606/88 |
| 2015/0190143 A1* | 7/2015 | Tarabichi | A61B 17/154 623/20.36 |
| 2016/0157751 A1* | 6/2016 | Mahfouz | A61B 5/062 600/409 |
| 2017/0143494 A1* | 5/2017 | Mahfouz | A61B 34/20 |
| 2018/0253838 A1* | 9/2018 | Sperling | A61B 5/0035 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |

(56) References Cited

FOREIGN PATENT DOCUMENTS

| | | |
|---|---|---|
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

\* cited by examiner

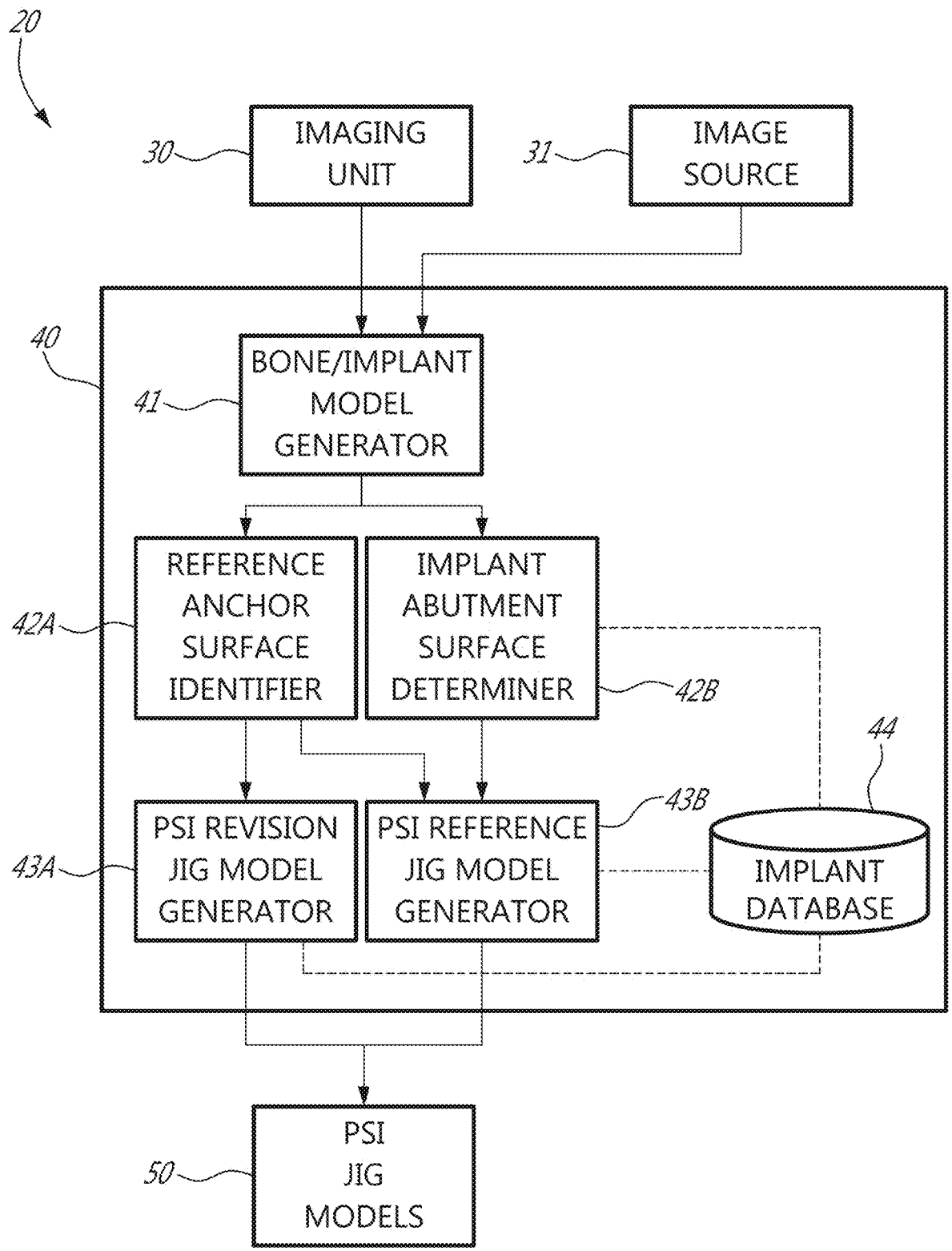

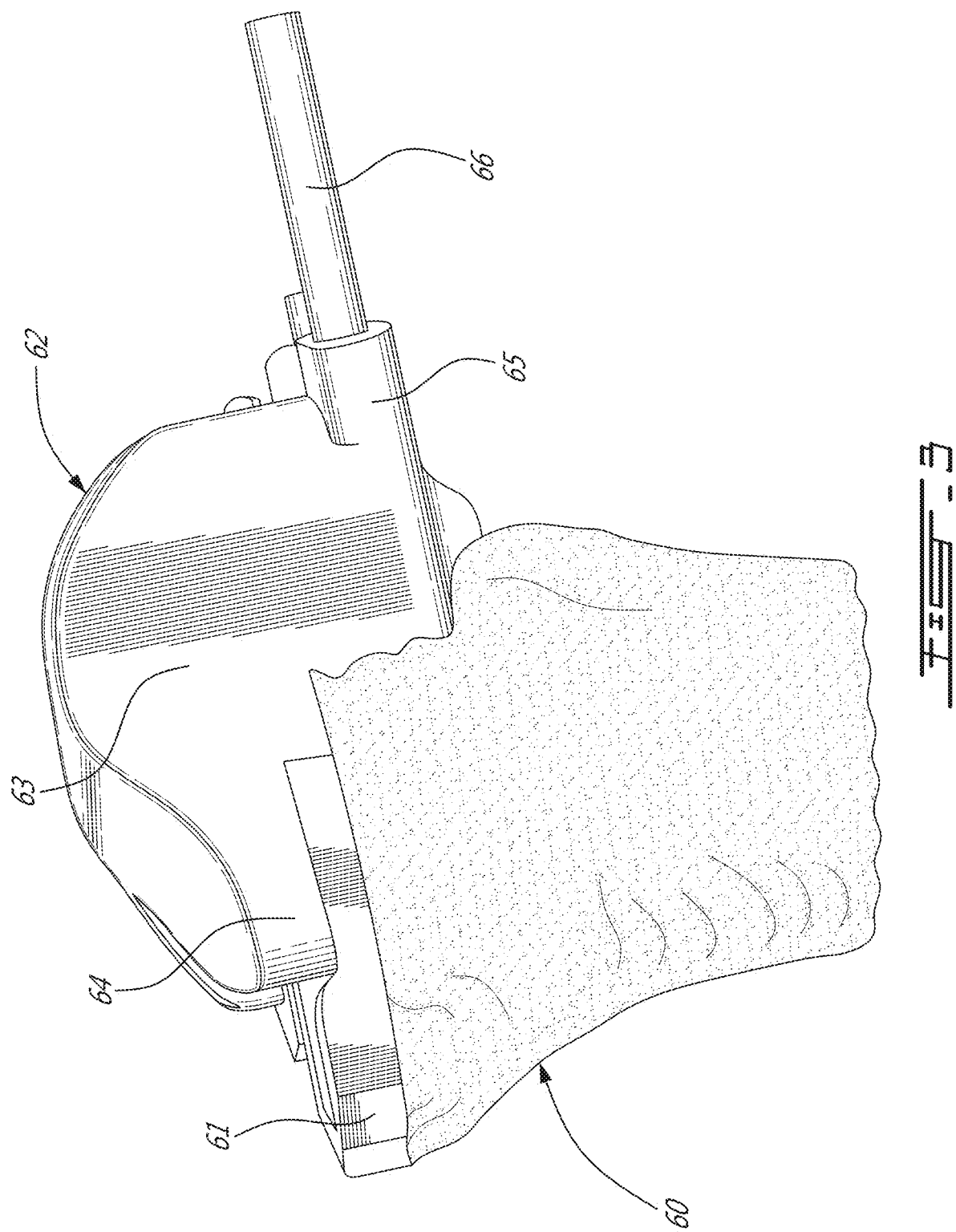

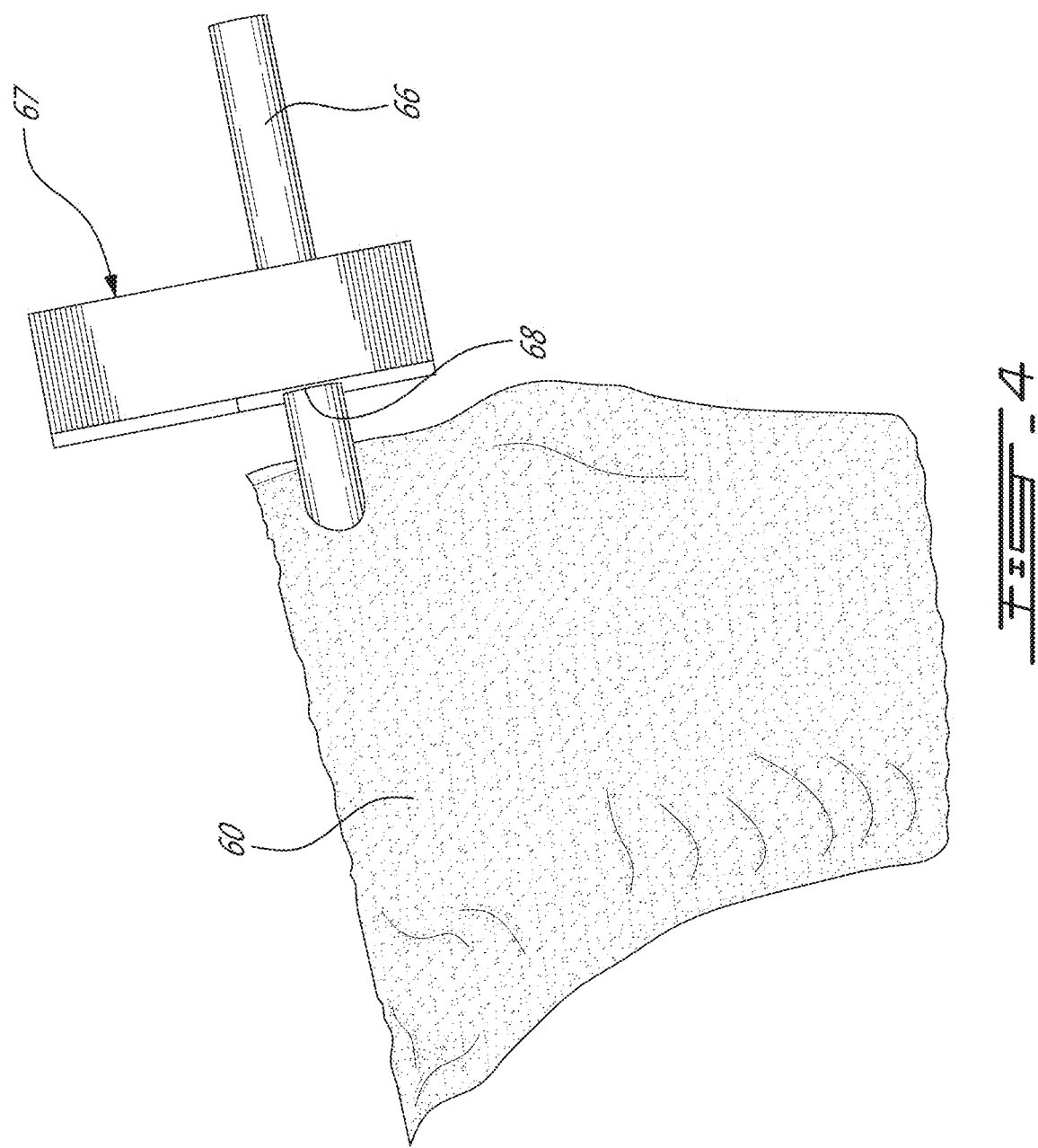

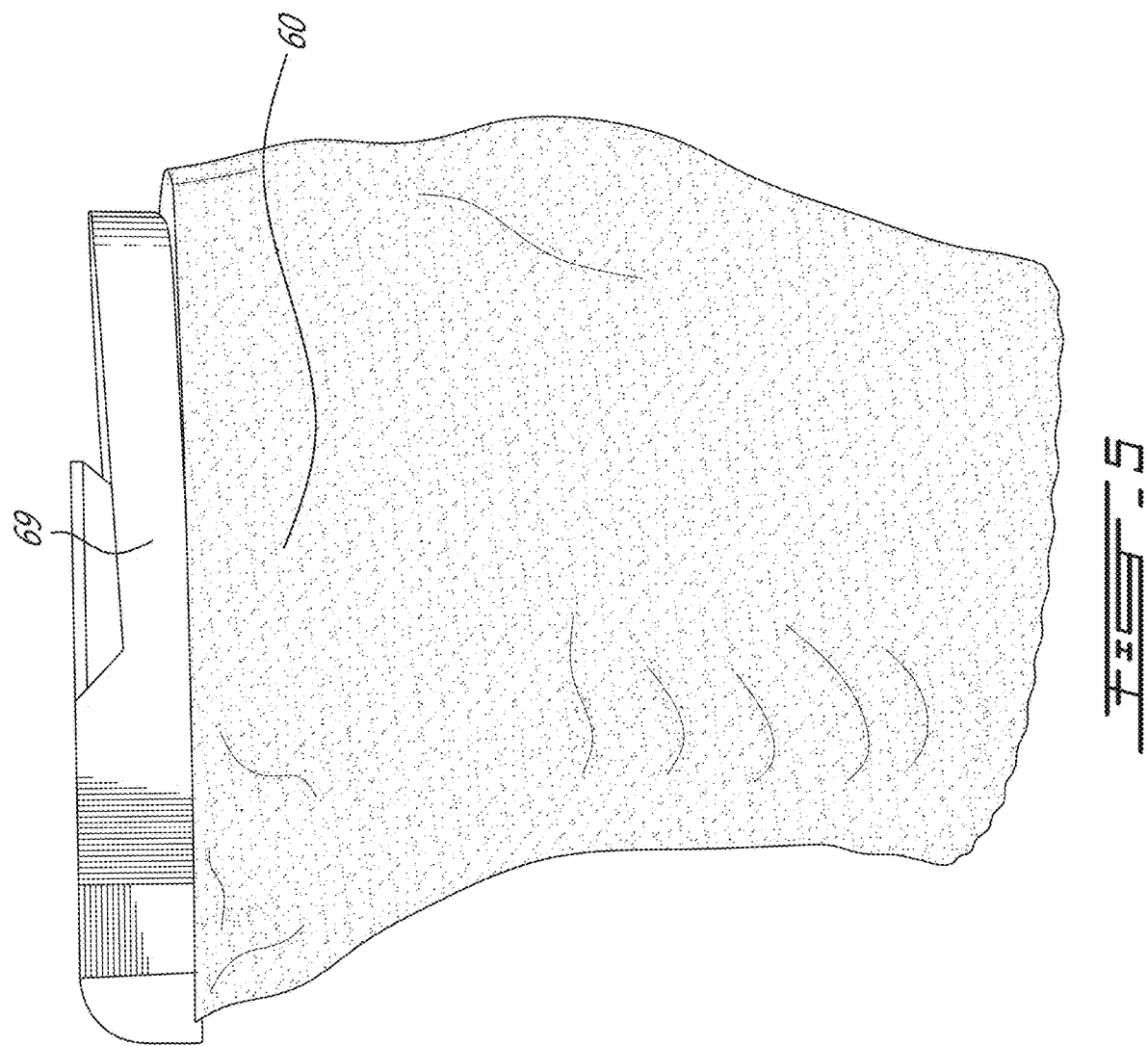

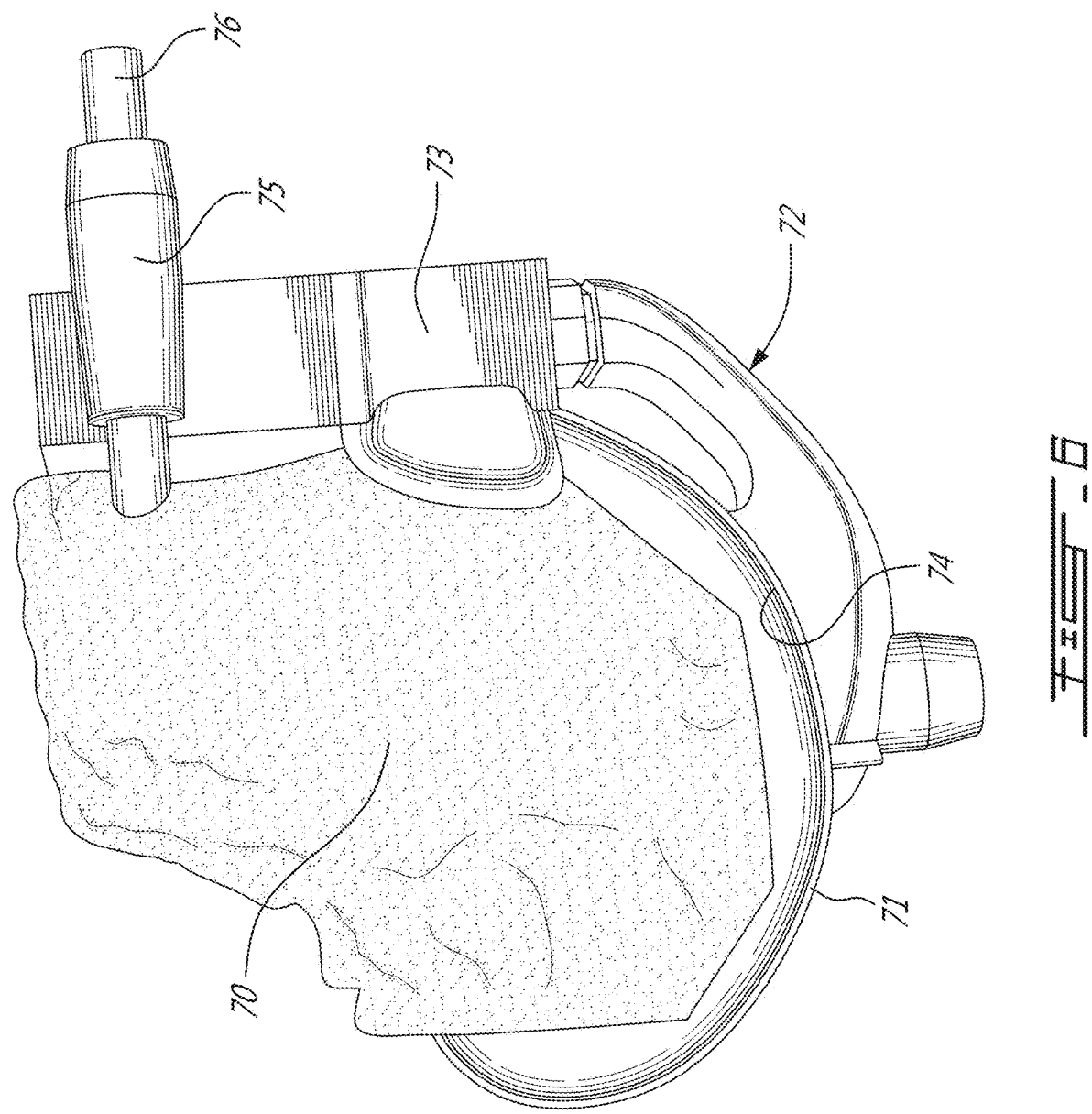

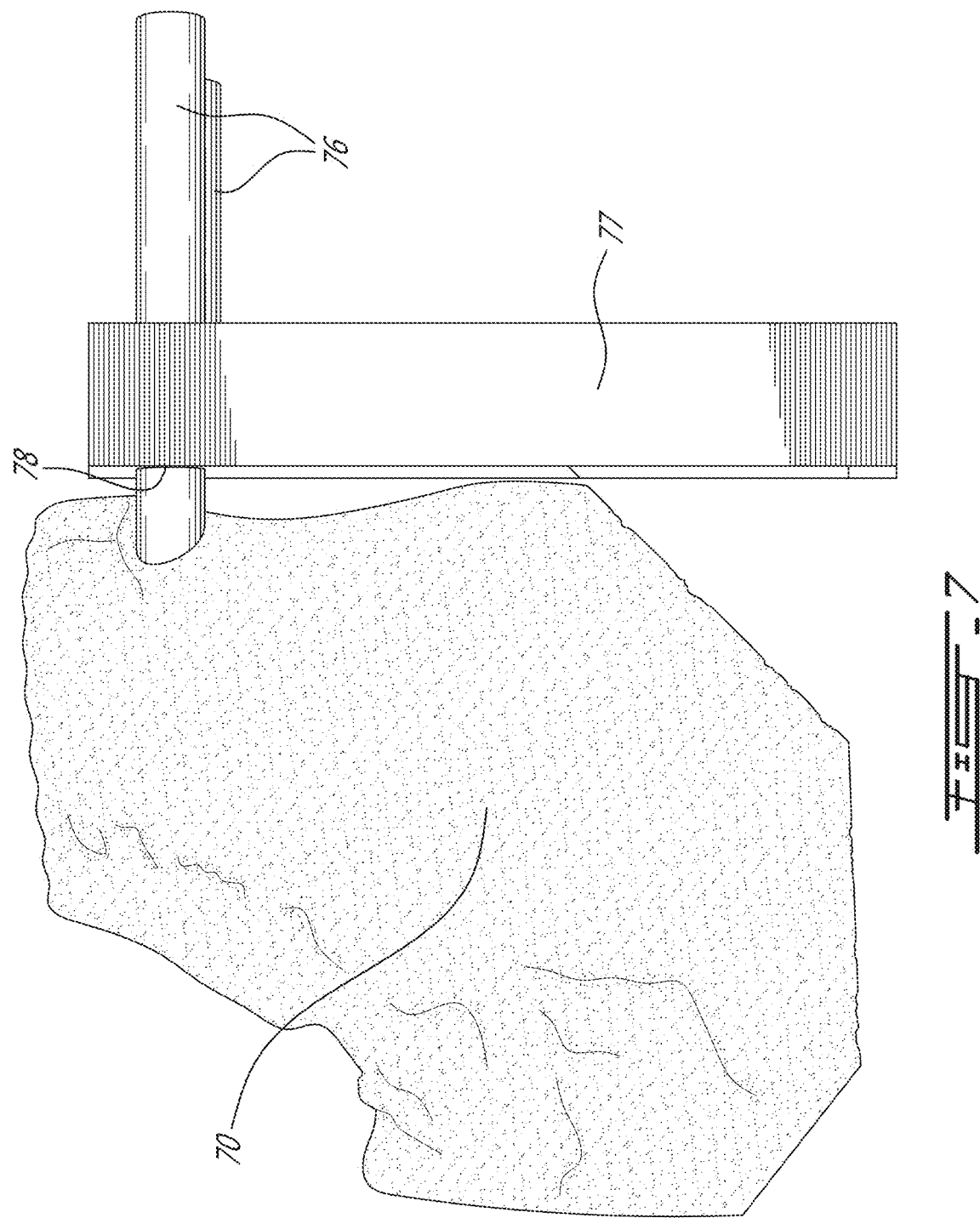

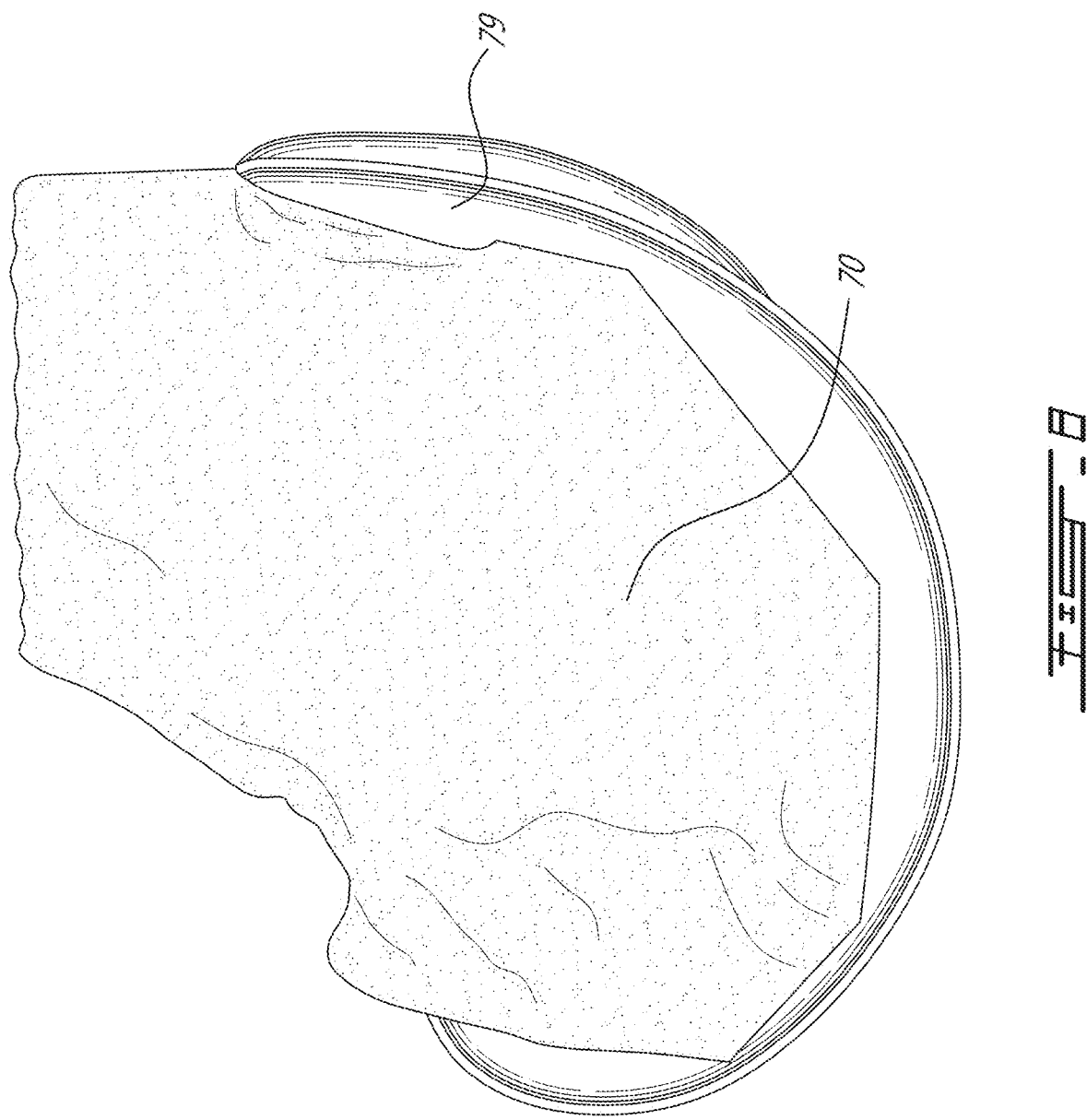

PATENT-SPECIFIC INSTRUMENTATION FOR IMPLANT REVISION SURGERY

CROSS-REFERENCE TO RELATED APPLICATIONS

The present application claims the priority of U.S. Patent Application No. 62/189,941, filed on Jul. 8, 2015, which is incorporated by reference in its entirety.

FIELD OF THE INVENTION

The present disclosure pertains to patient specific instrumentation (PSI) used in orthopedic surgery and, more particularly, to PSI used for implant revision.

BACKGROUND OF THE INVENTION

An implant revision surgery is a process by which an existing implant is removed to be replaced by a new implant. However, due to the bond between the implant to be removed and the bone, the bone is often damaged during implant removal. As a result, the subsequent positioning and installation of a replacement implant may lack precision due to damaged bone surfaces. For instance, in knee revision surgery, machining of the bone surfaces using conventional cutting blocks may lack precision as conventional bone landmarks used for defining the orientation of the cutting block may be altered or removed during the removal of the implant.

Patient specific instrumentation (hereinafter "PSI") pertains to the creation of instruments that are made specifically for the patient. PSI are typically manufactured from data using imaging to model bone geometry. Therefore, PSI have surfaces that may contact the bone in a predictable way as such contact surfaces are specifically manufactured to match the surface of a bone of a given patient. It would therefore be desirable to use PSI technology in an implant revision process.

SUMMARY OF THE DISCLOSURE

It is an aim of the present disclosure to provide a method for creating a PSI jig for implant revision surgery.

It is a further aim of the present disclosure to provide a system for creating a PSI implant revision jig model.

Therefore, in accordance with a first embodiment of the present disclosure, there is provided a method for creating at least one model of a patient-specific instrumentation jig for implant revision using a processing system, comprising: obtaining at least one image of at least part of a bone requiring implant revision and of an implanted implant on the bone, the at least one image being patient specific; identifying at least one reference anchor surface on the bone from the at least one image of the bone, the reference anchor surface configured to receive at least one guide reference; determining an implant abutment surface on the implanted implant; and generating and outputting a virtual reference jig model using at least the identified reference anchor surface and the determined implant abutment surface, the reference jig model comprising at least one contact surface corresponding to the determined implant abutment surface for complementary connection with the determined implant abutment surface, at least one guide interfacing portion configured to guide a planting of the at least one guide reference in the reference anchor surface, and a patient-specific geometry between the at least one contact surface and the at least one guide interfacing portion, to the patient-specific geometry adapted to position and/or orient the at least one guide interfacing portion relative to the at least one reference anchor surface, during the planting of the at least one guide reference in the at least one reference anchor surface, when the at least one contact surface is complementarily connected with the determined implant abutment surface.

Further in accordance with the first embodiment, a revision jig model is in some instances generated using at least the position and orientation of the at least one guide reference and a virtual model of a replacement implant, the jig model comprising at least one guide interfacing portion configured to engage the at least one guide reference, at least one tool interface portion positioned and/or oriented relative to the guide reference and at least one patient-specific geometry between the at least one guide interfacing portion of the jig model and the at least one tool interface portion, the at least one tool interface portion adapted to be interfaced with a tool altering the bone to perform cuts for subsequently installing the replacement implant.

Still further in accordance with the first embodiment, generating the revision jig model comprises in some instances creating a bone contact surface configured to contact the reference anchor surface.

Still further in accordance with the first embodiment, generating and outputting the reference jig model comprises in some instances using a virtual model of a replacement implant, a planned position of the replacement implant, and a virtual model of a stock revision jig to create the patient-specific geometry of the reference jig model.

Still further in accordance with the first embodiment, obtaining the at least one image comprises in some instances obtaining radiographic images only.

Still further in accordance with the first embodiment, generating the reference jig model comprises in some instances obtaining a virtual 3D model of the implanted implant for creating the at least one contact surface.

Still further in accordance with the first embodiment, creating the at least one contact surface comprises in some instances creating a negative surface of a portion of the implant abutment surface.

Still further in accordance with the first embodiment, the at least one guide reference is in some instances a pair of guide pins, and wherein generating the reference jig model comprises in some instances defining pin guides in the at least one guide interfacing portion.

Still further in accordance with the first embodiment, identifying the at least one reference anchor surface on the bone comprises in some instances identifying one of the medial epiphyseal bone and the anterior cortex from a femur.

Still further in accordance with the first embodiment, identifying the at least one reference anchor surface on the bone comprises in some instances identifying one of the medial aspect, the lateral aspect and the superior tubercle from a tibia.

Still further in accordance with the first embodiment, generating and outputting a virtual reference jig model comprises in some instances generating and outputting at least one of an additive printing instructions model and a numerical control machining instructions model.

Still further in accordance with the first embodiment, the at least one patient-specific instrumentation jig is in some instances fabricated.

In accordance with a second embodiment of the present disclosure, there is provided a system for generating at least one patient specific instrumentation jig model for implant revision, comprising: a reference anchor surface identifying module configured to identify at least one reference anchor surface from at least one patient specific image of at least one portion of a bone and of an implanted implant, the reference anchor surface configured to receive at least one guide reference; an implant abutment surface determining module configured to determine at least one implant abutment surface from the patient specific bone image; and a PSI reference jig model generator module configured to generate and output a reference jig model using at least the identified reference anchor surface and the determined implant abutment surface, the reference jig model comprising at least one contact surface corresponding to the determined implant abutment surface for complementary connection with the determined implant abutment surface, at least one guide interfacing portion configured to guide a planting of the at least one guide reference in the reference anchor surface, and a patient-specific geometry between the at least one contact surface and the at least one guide interfacing portion, the patient-specific geometry adapted to position and/or orient the at least one guide interfacing portion relative to the at least one reference anchor surface, for during the planting of the at least one guide reference in the at least one reference anchor surface, when the at least one contact surface is complementarily connected with the determined implant abutment surface.

Further in accordance with the second embodiment, a PSI revision jig model generator module generates in some instances a revision jig model using at least the position and orientation of the at least one guide reference and a virtual model of a replacement implant, the jig model comprising in some instances at least one guide interfacing portion configured to engage the at least one guide reference, at least one tool interface portion positioned and/or oriented relative to the guide reference and at least one patient-specific geometry between the at least one guide interfacing portion of the jig model and the at least one tool interface portion, the at least one tool interface portion adapted to be interfaced with a tool altering the bone to perform cuts for subsequently installing the replacement implant.

Still further in accordance with the second embodiment, the PSI revision jig model generator module creates in some instances a contact surface for contact with the reference anchor surface.

Still further in accordance with the second embodiment, the PSI reference jig model generator module configured to use in some instances a virtual model of a replacement implant, a planned position of the replacement implant, and a virtual model of a stock revision jig to create the patient-specific geometry of the reference jig model.

Still further in accordance with the second embodiment, the at least one patient specific image comprises in some instances radiographic images only.

Still further in accordance with the second embodiment, the PSI reference jig model generator module is configured to obtain in some instances a virtual 3D model of the implanted implant to create the at least one contact surface.

Still further in accordance with the second embodiment, the PSI reference jig model generator module is configured to create in some instances the at least one contact surface by creating a negative surface of a portion of the implant abutment surface.

Still further in accordance with the second embodiment, the at least one guide reference in some instances comprises a pair of guide pins, and the PSI reference jig model generator module is configured to define pin guides in the at least one guide interfacing portion.

Still further in accordance with the second embodiment, the reference anchor surface identifying module is configured to identify in some instances the at least one reference anchor surface on the bone by identifying one of the medial epiphyseal bone and the anterior cortex from a femur.

Still further in accordance with the second embodiment, the reference anchor surface identifying module is configured to identify in some instances the at least one reference anchor surface on the bone by identifying one of the medial aspect, the lateral aspect and the superior tubercle from a tibia.

Still further in accordance with the second embodiment, the system is configured to generate and output in some instances at least one of an additive printing instructions model and a numerical control machining instructions model.

The feature or features of one embodiment may be applied to other embodiments, even though not described or illustrated, unless expressly prohibited by this disclosure or the nature of the embodiments.

Some details associated with the present embodiments are described above and others are described below.

BRIEF DESCRIPTION OF THE FIGURES

FIG. 2 is a block diagram showing a system for creating a PSI implant revision jig model in accordance with another embodiment of the present disclosure;

FIG. 3 is a perspective view of a tibia with a PSI reference jig thereon, to plant guide landmarks;

FIG. 4 is a perspective view of the tibia of FIG. 3, with a PSI revision jig on the guide landmarks;

FIG. 5 is a perspective view of the tibia of FIG. 4, with an implant after revision;

FIG. 6 is a perspective view of a femur with a PSI reference jig thereon, to plant guide landmarks;

FIG. 7 is a perspective view of the femur of FIG. 6, with a PSI revision jig on the guide landmarks; and FIG. 8 is a perspective view of the femur of FIG. 7, with an implant after revision.

DESCRIPTION OF THE PREFERRED EMBODIMENTS

Figure 1:
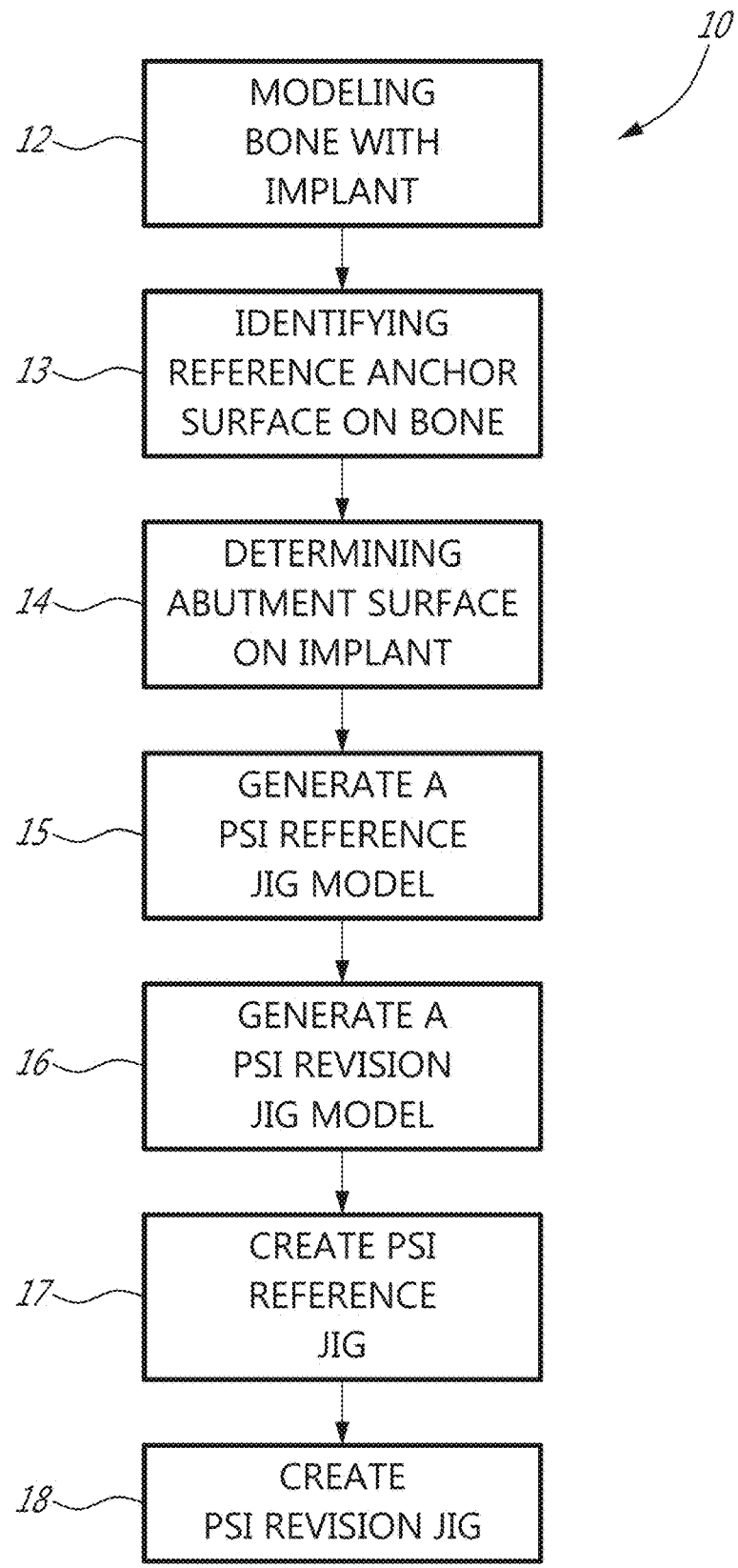
FIG. 1 is a flow chart showing a method for creating a PSI jig for implant revision in accordance with an embodiment of the present disclosure.

Referring to the drawings, and more particularly to FIG. 1, there is illustrated a method 10 for creating patient specific instrumentation (hereinafter PSI) jig for implant revision. For clarity, reference to patient specific in the present application pertains to the creation of negative corresponding surfaces, i.e., a surface that is the negative opposite of a patient bone/cartilage surface or implant, such that the patient specific surface conforms to the patient bone/cartilage surface, by complementary confirming contact. An instrument may also be patient specific in that it is used to plant guide references in a patient's bone, at a specific pre-planned location based on the patient's specific anatomy—the geometry of the instrument is specific and unique to the patient. The method is particularly suited to be used in knee revision in which the tibial knee implant, the femoral knee implant or both implants need to be replaced. The method may also be used in other orthopedic implant revision surgery, for instance in shoulder revision surgery.

According to 12, the bone and its implant are modeled. The models may be obtained and/or generated using imaging. The imaging may be done by any appropriate technology such as CT scanning (computerized tomography), fluoroscopy, or like radiography methods, providing suitable resolution of images. The model of the bone comprises a surface geometry of parts of the bone that are exposed despite the presence of the implant and/or the limitations of the imaging. The model of the bone may include a surface geometry of the implant relative to adjacent bone surfaces, and a 3D geometry of the implant, for instance using a 3D model of implant (e.g., from the manufacturer, etc). In particular, a combination of radiography and magnetic resonance imagery (MRI) may provide a suitable resolution between implant, bone and cartilage, useful to recognize the boundaries of the implant relative to the bone. The images of the implant may be confirmed, or the model improved using the manufacturer's model of the existing implant. In an embodiment, the method is performed using exclusively radiographic images of the bone and implant. As described hereinafter, PSI jigs will abut directly against the implants being replaced, to position reference landmarks in the bone, whereby radiographic images may provide, on their own, suitable resolution to create the PSI jigs. The radiographic images may also assist in performing a surface matching operation to merge the manufacturer's 3D virtual model of the implant with the bone imaging, if desired.

The bone modeling may comprise generating a 3D surface of the bone if the bone modeling is not directly performed by the imaging equipment, or if not complete. In the instance in which multiple implants must be replaced (e.g., total knee revision), all bones supporting implants are modeled. Additional structures may be modeled as well, such as cartilage, etc.

The model of the bone and implanted implant provides data that may be used by an operator, such as a surgeon, to plan revision surgery. In terms of planning, the operator may select the position and orientation of a 3D model of a replacement implant (i.e., a new implant) that will be used in revision surgery by looking at the model and/or may determine locations for cut planes to support the replacement implant. Factors that may come into consideration include orientation in frontal, sagittal and axial plane, native joint line, implanted implant joint line, bone damage, among other factors. Moreover, additional data such as a pre-operative kinematic analysis of the joint, and soft tissue tension, may be part of the data that may be available for the planning of the revision surgery, and may assist in determining a revised implant position and orientation.

According to 13, reference anchor surfaces are identified on the bone from the model(s) of 12. The reference anchor surfaces are selected as being sufficiently solid to support references such as pins or screws, and as not being altered by the removal of the used implant from the bone. For example, in the case of femoral knee revision, the reference anchor surfaces may be the medial epiphyseal bone and the anterior cortex. The epicondyles may be used to restore the joint line to set the axial position of the replacement implant. Other parts of the femur may also be used as reference anchor surfaces.

As another example, in the case of tibial knee implant replacement, the reference anchor surfaces may be that of the medial and lateral aspects as well as the superior tubercle portion of the tibia. In this case, the medial and lateral aspects may be used to restore the joint line by setting the axial position of the replacement implant. Other parts of the tibia may also be used as anchor surfaces. Similar considerations are taken into account in the case of shoulder surgery. In both cases, the anchor surfaces are in close proximity to the implanted implant (the implant already present, but to be removed in the revision process, also referred to as used implant or removed implant) as it is in the vicinity of the removed implant that bone alterations will be performed. Although the reference anchor surface(s) is in close proximity to the removed implant, the anchor surface will not substantially be damaged by the removal of the used implant.

In another embodiment, other factors influencing the selection of the reference anchor surface(s) are the planned location of the replacement implant, of the cut planes, and the geometry of stock/generic cutting blocks.

According to 14, an abutment surface on the implanted implant is determined, for subsequent support of a PSI reference jig that is used to plant the guide references. As the implanted implant has a known geometry—via the manufacturer's model and the modeling of 12—, the implanted implant is an available support for a PSI instrument before it is removed. The implanted implant not only has a known geometry, but also forms the joint surface of the articulation, whereby it may be a strategic PSI instrument support to ensure accuracy in reference placement.

The determination of the implant abutment surface takes into account the location of the guide reference(s), the implant abutment surface being for instance in relatively close proximity to the reference anchor surfaces. Other factors taken into consideration in the determination include any wear on the surface of implant, which worn implant surface may be avoided to use instead unaltered parts of the implant, which unaltered parts would match the manufacturer's model of the implant. A negative-contour matching surface could hence be based directly on the manufacturer's model, for being applied against the implanted implant.

According to 15, using the reference anchor surface(s) identified in 13, and the implant abutment surface(s) determined in 14, a PSI reference jig model is generated. The jig model will have a contact surface(s) defined to abut against the implant abutment surface(s) obtained in 14, in a predictable and precise manner. Moreover, the PSI reference jig model may have guiding features (e.g., guide holes) to guide an operator in anchoring the guide references in the bone, such that the guide references are at the planned position and orientation.

In an embodiment, the PSI reference jig model is generated to enable the subsequent use of stock cutting jigs. In such a case, the PSI reference jig model is devised taking into consideration the geometry of the planned location of the replacement implant, of the cut planes, and the geometry of stock/generic cutting blocks. The PSI reference jig model may be in any appropriate format, such as an additive printing execution file or model, a numerical control machining file, etc.

According to 16, using the position and orientation of the guide references, the geometry of the replacement implant that is known (i.e., obtained from a database, from the manufacturer, generated as a PSI implant, etc), and possibly the reference anchor surfaces as obtained from the bone model(s), a PSI revision jig model may be generated, as an alternative to using a stock/generic cutting jig. The jig model will have a guide interfacing portion adapted to be connected to the guide landmarks. The jig model may also have a contact surface(s) defined to abut against the reference anchor surface(s) obtained in 13, in a predictable and precise manner, with this contact surface not necessarily but possibly being a negative contour surface. Typically, the PSI revision jig is a cutting block or cutting guide that will allow planes to be cut upon which will be anchored the implant.

The PSI revision jig model of 16 therefore comprises cutting planes, guides, slots, or any other tooling interface or tool, oriented and/or positioned to allow bone alterations to be formed in a desired location of the bone, relative to the contact surface(s). Thus, PSI revision jig model may also take into consideration any revision planning done by the operator (e.g., surgeon), to therefore allow the removal of sufficient bone material to reproduce desired gaps between cut planes on adjacent bones, etc. The PSI revision jig model may be in any appropriate format, such as an additive printing execution file or model, a numerical control machining file, etc.

According to 17, once the PSI reference jig model has been generated, the PSI reference jig may be created, with numerical control machining, additive printing, a combination thereof and/or any other suitable method. When installing the PSI reference jig on the implanted implant bone, the contact surface(s) on the PSI jig is(are) applied against the corresponding implant abutment surface(s) of 14, with a unique complementary match that will ensure that the planned positioning is reached. The operator can then use the PSI reference jig to position the guide reference(s) in the reference anchor surface(s) as planned.

According to 18, once the PSI revision jig model has been generated, the PSI revision jig may be created, if such a PSI jig is used instead of a stock cutting jig. If the PSI revision jig is created, it may be done by numerical control machining, additive printing, a combination thereof and/or any other suitable method. When installing the PSI revision jig on the bone, the jig will be mounted onto the guide references (e.g., pins, screws), and therefore has another guide interfacing portion. It may also be desired that a contact surface(s) on the PSI revision jig is(are) applied against the anchor surface(s) of 13. The PSI jig created in 18 may then be used intra-operatively after the implant is removed to allow alterations to be made on the bone. For instance, in the case of total knee revision, jigs are used to perform femoral distal and tibial cuts.

While a specific order has been provided above, other orders are considered as well. For instance, it is contemplated to determine the abutment surface before identifying the reference anchor surfaces. Other step inversions are contemplated as well, for instance if a stock (i.e., non PSI) cutting jig is used.

Now that a method for creating a PSI reference jig and a PSI revision jig for implant replacement has been defined, a system is set forth.

A system for the creation of PSI jig models is generally shown at 20 in FIG. 2. The system 20 may comprise an imaging unit 30, such as a CT scan or an X-ray machine, so as to obtain images of the bone and implant. As an alternative, images may be obtained from an image source 31. As an example, a CT scan may be operated remotely from the system 20, whereby the system 20 may simply obtain images and/or processed bone and implant models from the image source 31.

The system 20 comprises a processor unit 40 (e.g., computer, laptop, etc.) that comprises different modules so as to ultimately produce a jig model(s). The processing unit 40 of the system 20 may therefore comprise a bone/implant model generator 41 receiving images from sources 30 or 31 to generate a 3D model of the bone with the implant, prior to implant revision. In accordance with the method 10 of FIG. 1, the 3D model of the bone with implant may comprise data pertaining to the surface geometry of a relevant portion of a bone and of the implant, including surfaces of the bone that are exposed despite the presence of the implant.

The bone/implant model generator 41 will create the 3D model of the bone and implant that is then used by a reference anchor surface identifying module 42A and an implant abutment surface determining module 42B of the processing unit 40. Alternatively, the modules 42A and 42B may use a 3D model provided by the image source 31, provided the model obtained from the image source 31 comprises sufficient data. The virtual 3D model of the bone and implant may be generated using the manufacturer's model of the implant, whether it be via the image source 31 or via the bone/implant model generator 41.

The reference anchor surface identifier 42A identifies surfaces on the bone that may substantially not be altered by the removal of the damaged implant. The reference anchor surface(s) is(are) selected as being sufficiently solid to serve as support for guide landmarks such as pins of screws, and as not obstructing the removal of the implant. For example, reference is made to step 13, in which examples are provided for appropriate reference anchor surfaces on the femur and the tibia in the case of total knee replacement. The reference anchor surface identifier 42A may identify the reference anchor surface using planned cut planes and/or planned replacement implant geometry and position and orientation, as well as stock cutting jig geometry.

The implant abutment surface determining module 42B identifies abutment surfaces on the implant that will serve as support for a PSI reference jig, to plant the guide landmarks in the bone surfaces identified by the reference anchor surface identifier 42A. For example, reference is made to step 14, in which examples are provided for appropriate implant abutment surfaces. The implant abutment surface determining module 42B may provide target implant abutment surface(s) for the operator to participate in the selection.

Once the reference anchor surface(s) is(are) identified and the implant abutment surface are determined, a PSI revision jig model generator module 43A may generate a revision jig model (unless a stock cutting jig is used), whereas a PSI reference jig model generator module 43B will generate a reference jig model. As in 16 and 17 of the method 10, the reference jig model will have a contact surface(s) defined to abut against the implant determined by the module 42B, in a predictable and precise manner, for the planting of guide references. The revision jig model will have a guide interfacing portion to be mounted to the guide references, and may also be devised to contact the reference anchor surface. As the PSI revision jig will support a tool to perform alterations on the bone, the jig model comprises cutting planes, guides, slots, or any other tooling interface or tool, trackers, oriented and/or positioned to allow bone alterations to be formed in a desired location of the bone, relative to the contact surface(s).

Thus, jig model generator modules 43A and 43B may also take into consideration any revision planning done by the operator (e.g., surgeon). The jig model generator modules 43A and 43B may also take into consideration a geometry of the existing damaged implant, the replacement implant (e.g., obtained from an implant database 44), in addition to the anchor surface(s).

Accordingly, the system 20 outputs PSI jig model(s) 50 that will be used to create the PSI reference jig and optionally the PSI revision jig. The PSI reference jig serves to place the guide references while the PSI revision jig, or alternatively a stock cutting jig, is then used intra-operatively to resurface bone for subsequent implant installation, based on the positioning and path of the guide references, as described for method 10 in FIG. 1.

Exemplary embodiments are now provided, with a tibial application and a femoral application, among numerous other possibilities.

Referring concurrently to FIGS. 3-5, a knee portion of a tibia is generally shown at 60, with an implanted implant 61, to be revised. A PSI reference jig 62 has a body 63 having a geometry specific to the patient, to space in a given position and orientation a PSI contact surface 64 from a guide interfacing portion 65 as planned. Hence, the guide references, shown as pins 66, are planted in the reference anchor surface, shown in the embodiment as the posterior face of the tibia 60. The PSI contact surface 64 of the jig 62 abuts against a tibial plateau portion of the implant 61 in a unique complementary manner, and may also have PSI contact surfaces for abutment with the tibia 60, as observed.

Once the guide reference pins 66 are planted at FIG. 3, the PSI reference jig 62 may be removed, leaving the pins 66 positioned and oriented as planned. As shown in FIG. 4, the implanted implant 61 may be removed, and the PSI revision jig or stock cutting jig 67 may be slid onto the pins 66. The jig 67 is shown as a cutting block, defining cut slots or planes to remove parts of the tibia 60. The jig 67 may be patient specific by having a geometry to its body defined as a function of the patient's anatomy, for the cut slots or planes to be located based on the position of guide interfacing portion 68 (e.g., pin slots). Alternatively, the jig 67 may be a stock jig, the PSI reference jig 62 being configured to place the pins 66 in a given position for the jig 67 to be available from stock.

Referring to FIG. 5, once the cuts have been made using the jig 67, the pins 66 and the jig 67 may be removed, and a revised implant 69 may be installed.

Referring concurrently to FIGS. 6-8, a femur is generally shown at 70, at the knee joint, with an implanted implant 71, to be revised. A PSI reference jig 72 has a body 73 having a geometry specific to the patient, to position and orient a PSI contact surface 74 relative to a guide interfacing portion 75 based on pre-operative planning. Hence, the guide references, shown as pins 76, are planted in the reference anchor surface, shown in the embodiment as the anterior face of the femur 70. The PSI contact surface 74 of the jig 72 abuts against a distal end of the implant 71, and may also have PSI contact surfaces for abutment with the femur 70, as observed.

Once the guide reference pins 76 are planted at FIG. 6, the PSI reference jig 72 may be removed, leaving the pins 76 positioned and oriented as planned. As shown in FIG. 7, the implanted implant 71 may be removed, and the PSI revision jig or stock cutting jig 77 may be slid onto the pins 76. The jig 77 is shown as a cutting block, defining cut slots or planes to remove parts of the femur 70. The jig 77 may be patient specific by having the geometry of its body defined as a function of the patient's anatomy, for the cut slots or planes to be located based on the position of guide interfacing portion 78, with abutment against the femur 70 if desired.

Referring to FIG. 8, once the cuts have been made using the jig 77, the pins 76 and the jig 77 may be removed, and a revised implant 79 may be installed.

It is considered to use the reference guides as guides for a robotic arm to cut the planes on the bone. In such a case, no revision jig model would be required. Instead, a navigation file could be provided for a robotic system to perform surgery based on the placement on the reference guides.

While the methods and systems described above have been described and shown with reference to particular steps performed in a particular order, these steps may be combined, subdivided or reordered to form an equivalent method without departing from the teachings of the present disclosure. Accordingly, the order and grouping of the steps is not a limitation of the present disclosure.

The invention claimed is:

1. A method for creating at least one model of a patient-specific instrumentation jig for implant revision using a processing system, comprising:
    obtaining at least one image of at least part of a bone requiring implant revision and of an implanted implant on the bone, the at least one image being patient specific;
    identifying at least one reference anchor surface on the bone from the at least one image of the bone, the reference anchor surface configured to receive at least one guide reference;
    determining an implant abutment surface on the implanted implant; and
    generating and outputting a virtual reference jig model using at least the identified reference anchor surface and the determined implant abutment surface, the reference jig model comprising at least one contact surface corresponding to the determined implant abutment surface for complementary connection with the determined implant abutment surface, at least one guide interfacing portion configured to guide a planting of the at least one guide reference in the reference anchor surface, and a body interconnecting the at least one contact surface and the at least one guide interfacing portion, the body having a patient-specific geometry between the at least one contact surface and the at least one guide interfacing portion, so as to position and/or orient the at least one guide interfacing portion relative to the at least one reference anchor surface, for subsequently planting the at least one guide reference in the at least one reference anchor surface as identified when the at least one contact surface is complementarily connected with the determined implant abutment surface; and
    generating a revision jig model using at least the position and orientation of the at least one guide reference and a virtual model of a replacement implant, the jig model comprising at least another guide interfacing portion for engagement with the at least one guide reference, at least one tool interface portion positioned and/or oriented relative to the guide reference and at least one patient-specific geometry between the guide interfacing portion and the at least one tool interface portion, the at least one tool interface portion adapted to be interfaced with a tool altering the bone to perform cuts for subsequently installing the replacement implant.

2. The method according to claim 1, wherein generating the revision jig model comprises creating a bone contact surface for contact with the reference anchor surface.

3. The method according to claim 1, wherein generating and outputting the reference jig model comprises using a virtual model of a replacement implant and planned position thereof, and a virtual model of a stock revision jig to create the patient-specific geometry of the reference jig model.

4. The method according to claim 1, wherein obtaining the at least one image comprises obtaining radiographic images only.

5. The method according to claim 1, wherein generating the reference jig model comprises obtaining a virtual 3D model of the implanted implant for creating the at least one contact surface.

6. The method according to claim 5, wherein creating the at least one contact surface comprises creating a negative surface of a portion of the implant abutment surface.

7. The method according to claim 1, wherein the at least one guide reference is a pair of guide pins, and wherein generating the reference jig model comprises defining pin guides in the at least one guide interfacing portion.

8. The method according to claim 1, wherein identifying the at least one reference anchor surface on the bone comprises identifying one of the medial epiphyseal bone and the anterior cortex from a femur.

9. The method according to claim 1, wherein identifying the at least one reference anchor surface on the bone comprises identifying one of the medial aspect, the lateral aspect and the superior tubercle from a tibia.

10. The method according to claim 1, wherein creating the generating and outputting a virtual reference jig model comprises generating and outputting at least one of an additive printing instructions model and a numerical control machining instructions model.

11. The method according to claim 1, further comprising using the virtual reference jig model and/or the revision jig model to fabricate the at least one patient-specific instrumentation jig.

* * * * *